United States Patent [19]
Kontos

[11] Patent Number: 5,876,411
[45] Date of Patent: Mar. 2, 1999

[54] DEVICE AND METHOD FOR LOCATING AND SEALING A BLOOD VESSEL

[75] Inventor: Stavros Kontos, Woodcliff Lake, N.J.

[73] Assignee: X-Site L.L.C.

[21] Appl. No.: 814,221

[22] Filed: Mar. 11, 1997

[51] Int. Cl.[6] .................................................. A61B 17/04
[52] U.S. Cl. .......................... 606/144; 606/139; 606/145; 606/148
[58] Field of Search .................................. 606/139, 144, 606/145, 147, 148, 205, 207

[56] References Cited

U.S. PATENT DOCUMENTS

| | | | |
|---|---|---|---|
| 4,799,495 | 1/1989 | Hawkins et al. | 128/754 |
| 4,890,612 | 1/1990 | Kensey | 606/213 |
| 5,108,421 | 4/1992 | Fowler | 606/213 |
| 5,304,184 | 4/1994 | Hathaway et al. | 606/144 |
| 5,312,423 | 5/1994 | Rosenbluth et al. | 606/148 |
| 5,336,229 | 8/1994 | Noda | 606/144 |
| 5,336,231 | 8/1994 | Adair | 606/148 |
| 5,383,896 | 1/1995 | Gershony et al. | 606/213 |
| 5,391,183 | 2/1995 | Janzen et al. | 606/213 |
| 5,417,699 | 5/1995 | Klein et al. | 606/144 |
| 5,431,666 | 7/1995 | Sauer et al. | 606/139 |
| 5,447,502 | 9/1995 | Haaga | 604/265 |
| 5,527,322 | 6/1996 | Klein et al. | 606/144 |
| 5,613,974 | 3/1997 | Andreas et al. | |

Primary Examiner—Michael Buiz
Assistant Examiner—Tina T. D. Pham
Attorney, Agent, or Firm—Kenyon & Kenyon

[57] ABSTRACT

A device and a method for sealing an opening in an anatomical structure is provided. The device includes a flexible tube including a proximal portion and a distal portion extending along a common axis. The proximal portion is coupled to the distal portion by a central portion, which extends from a distal end of the proximal portion to a proximal end of the distal portion. The central portion bends away from the axis along a curve so that the distal end of the proximal portion faces the proximal end of the distal portion across a gap formed by the central portion. In use, the device is inserted through an opening in a wall of the anatomical structure so that a portion of the wall is received within the gap. A needle, that is attached to a first length of suture, is then inserted through a first needle lumen to an opening formed in the distal end of the proximal portion and crosses the gap penetrating the wall to enter a needle receiving chamber that is formed in the distal portion. The needle bends around the needle receiving chamber to exit the needle receiving chamber at a point opposite the second needle lumen. The needle is withdrawn from the structure via the second needle lumen and the device is rotated to a second position where a second length of suture is drawn through a second portion of the wall and secured to the first length of suture to seal the opening.

19 Claims, 14 Drawing Sheets

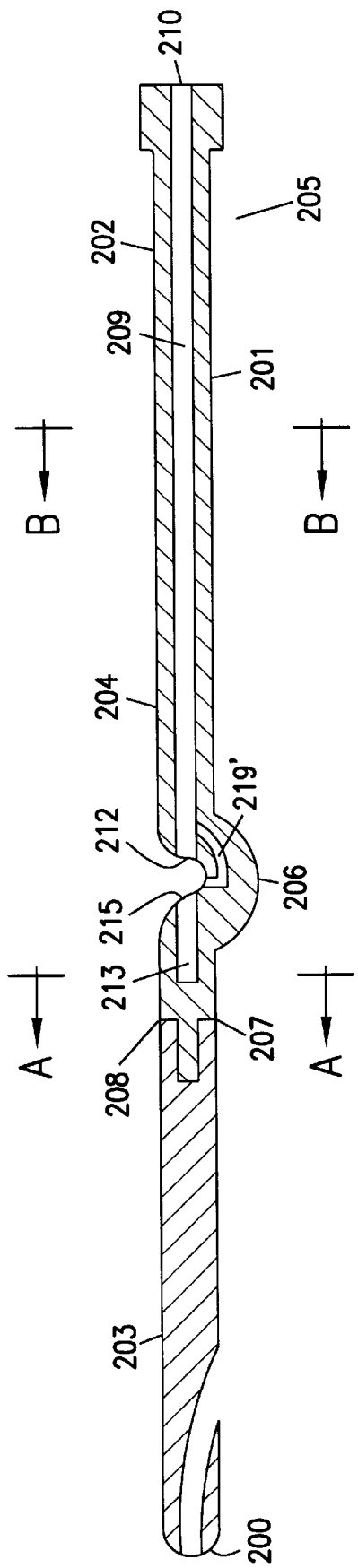
FIG. 1
FIG. 2A
FIG. 2B

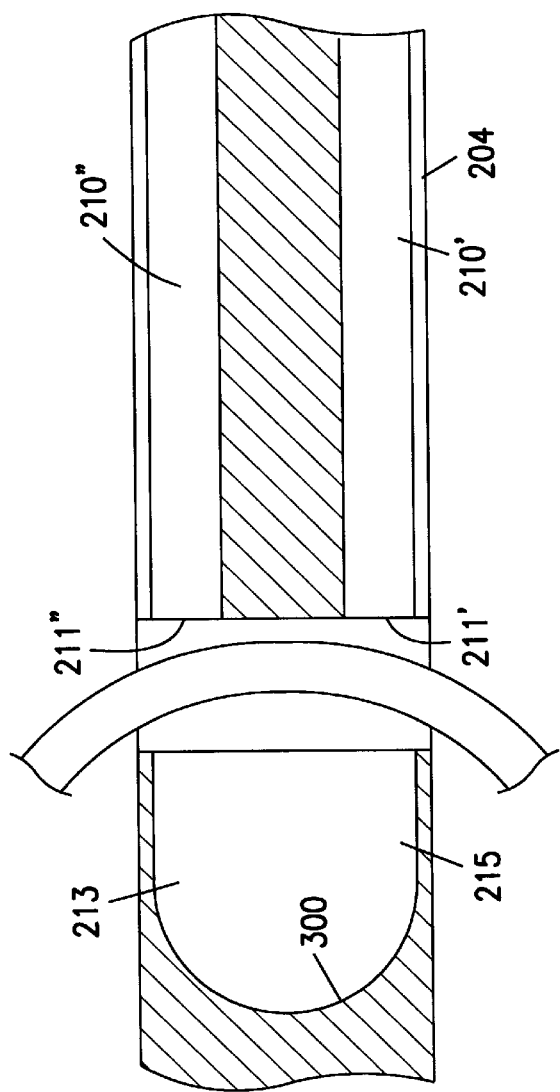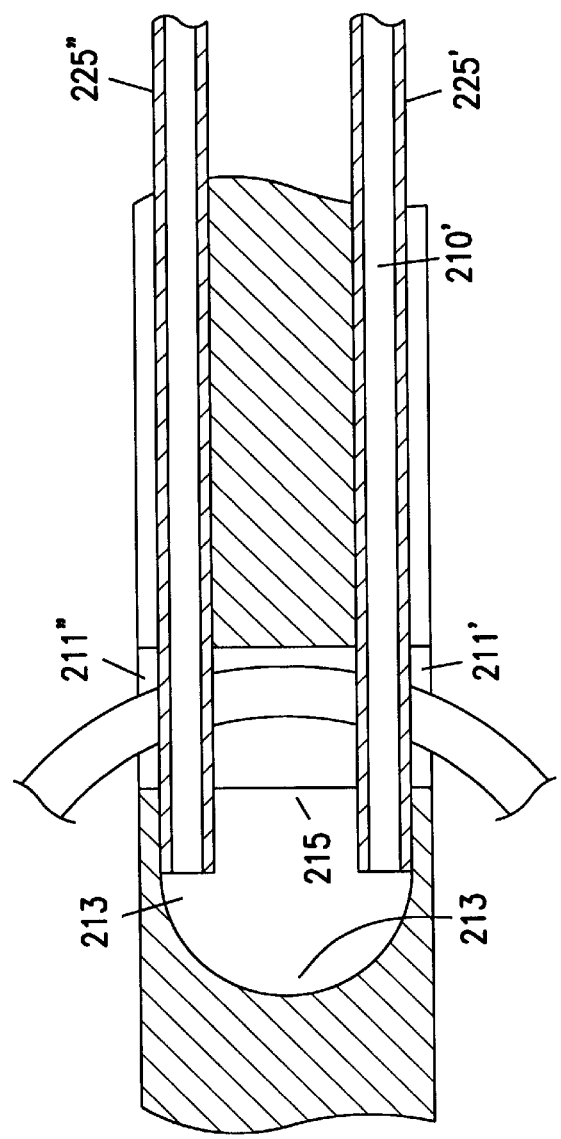

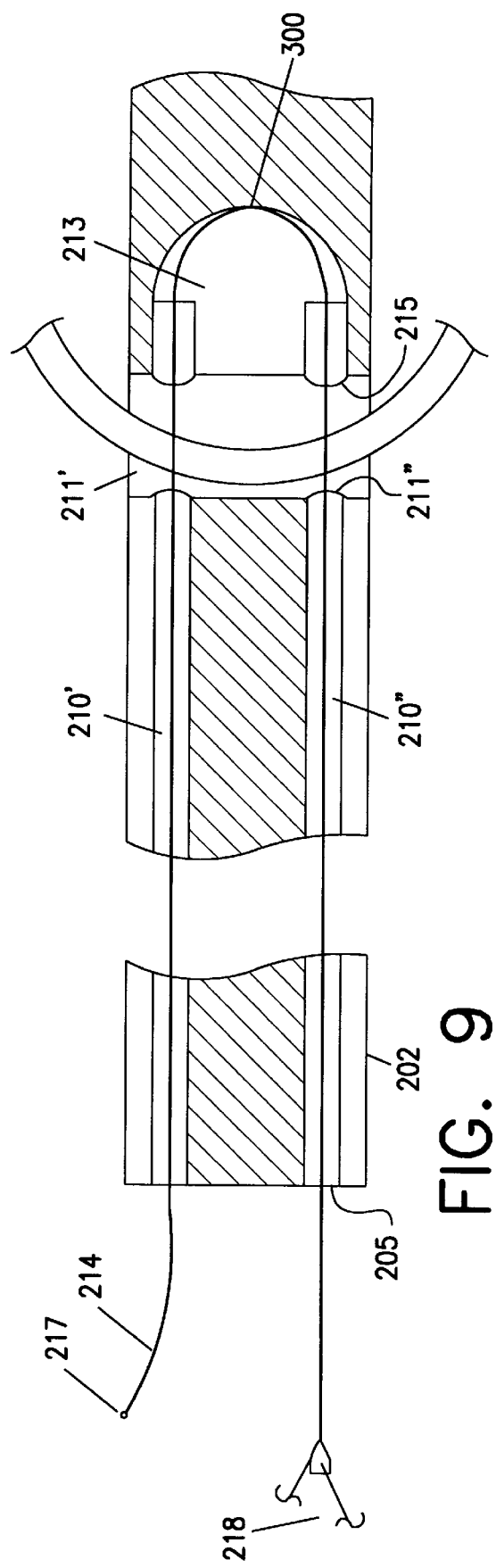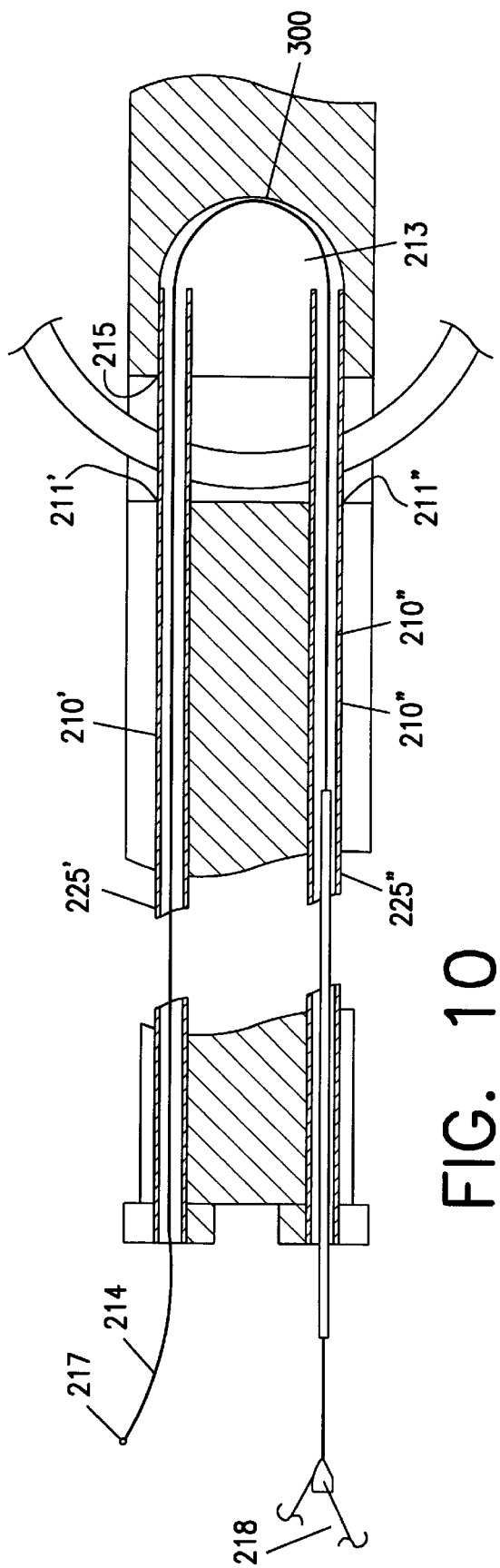

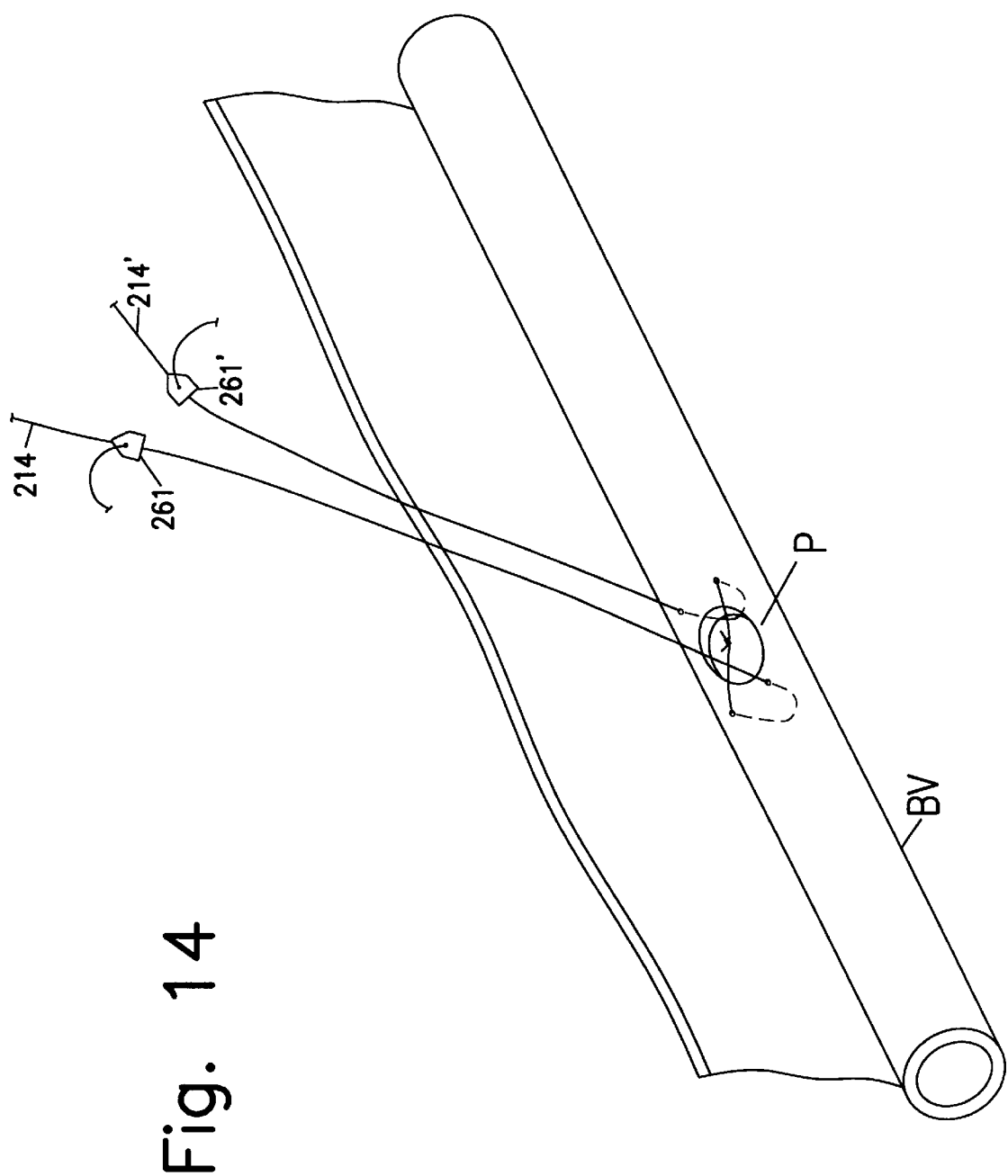

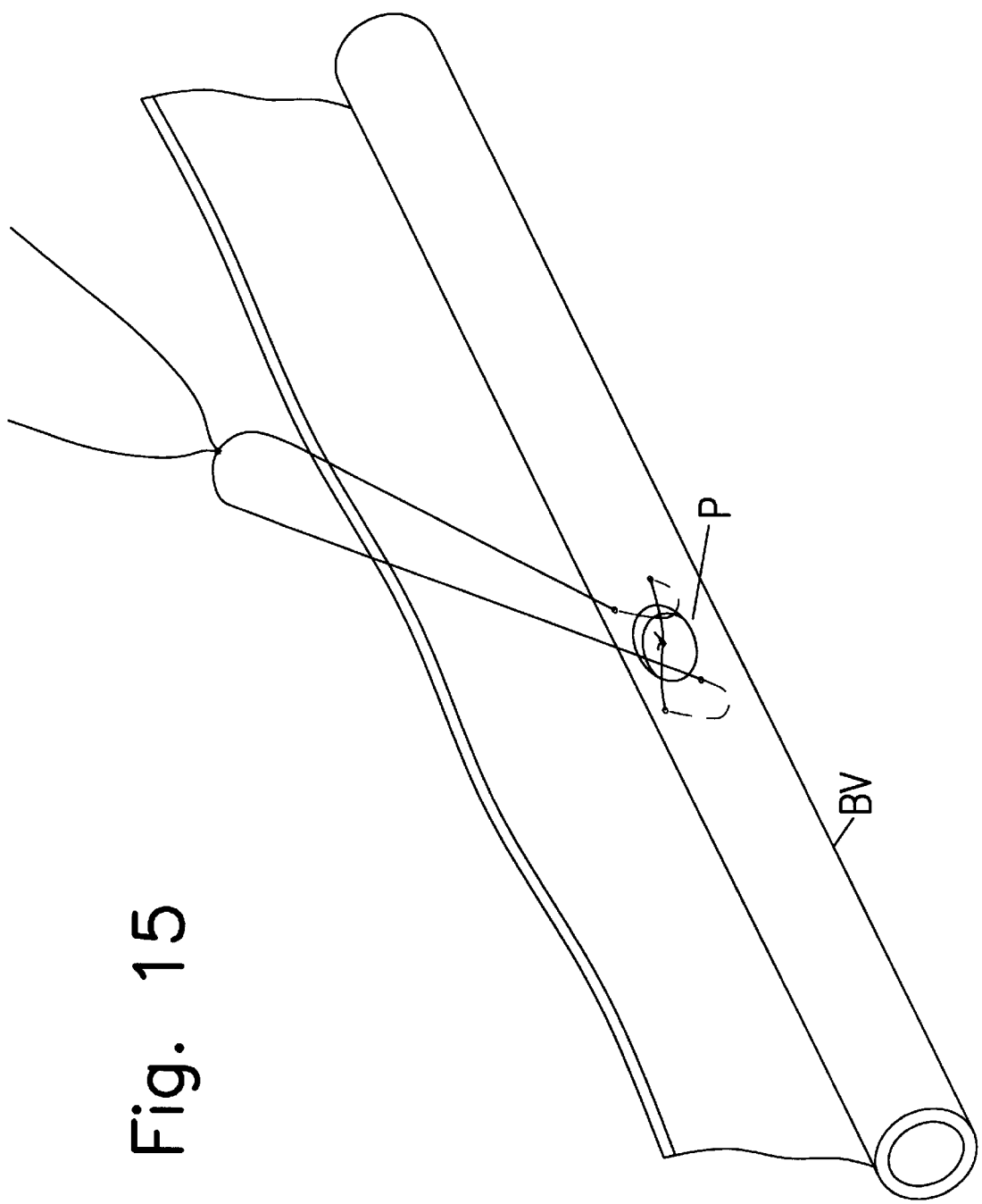

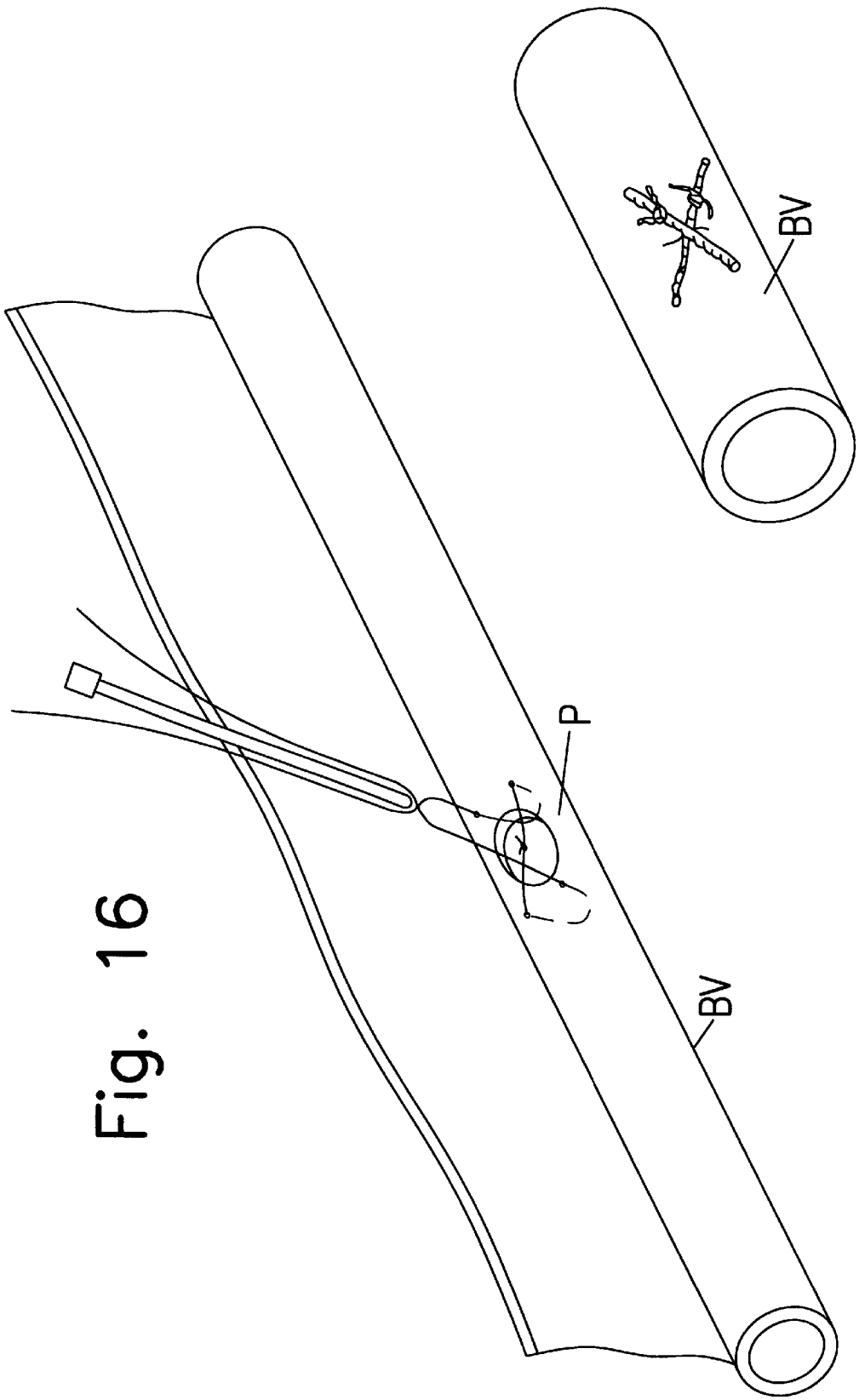

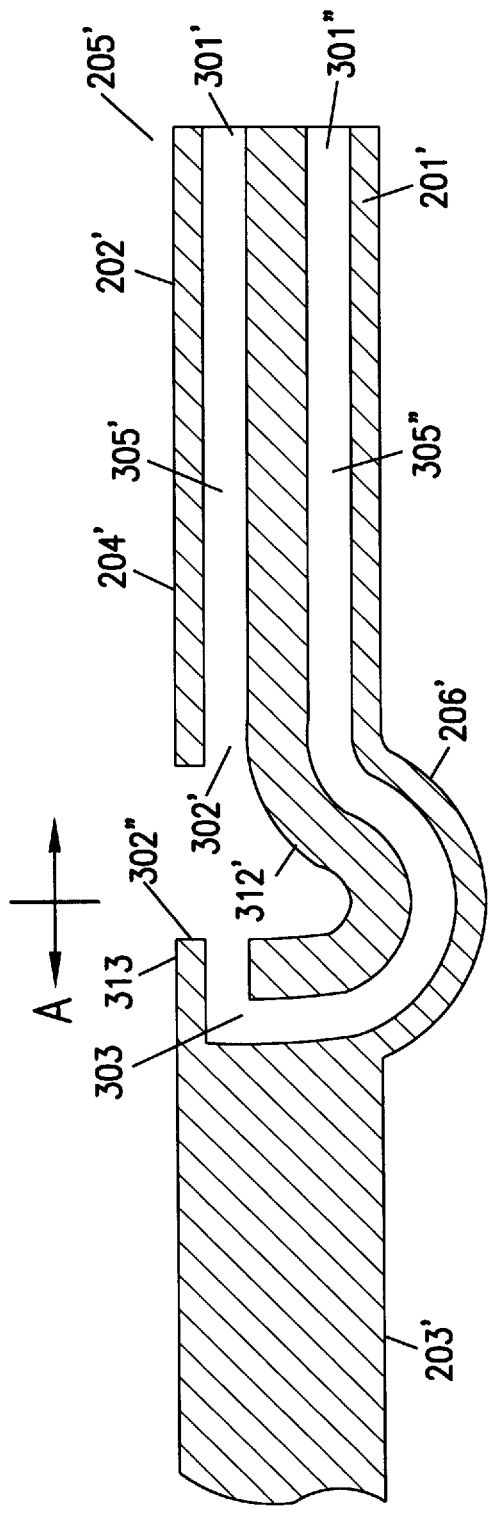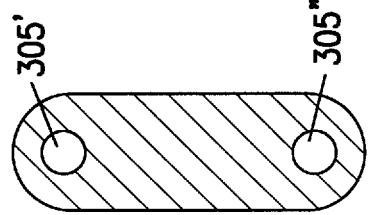

DEVICE AND METHOD FOR LOCATING AND SEALING A BLOOD VESSEL

FIELD OF THE INVENTION

The present invention relates generally to medical devices and, more particularly, to a method and device for sealing percutaneously formed punctures or incisions in a blood vessel.

BACKGROUND INVENTION

A physician must frequently close openings that are formed in blood vessels during various intravascular procedures. The openings are generally formed in order to allow intravascular instruments such as catheters to be inserted into the vessel. Once the procedure is completed, the opening (or openings) in the vessel is closed, often by applying and maintaining pressure on the skin until coagulation occurs. Effectuating such closures is time consuming for the physician and painful to the patient.

Devices for sealing punctured vessel walls with sutures are known in the art. For example, U.S. Pat. No. 4,890,612 describes a device for sealing a percutaneous puncture in a vessel that includes a tubular body with an expandable closure. The body has an ejecting means that forces the closure out of the body into the interior of the blood vessel, whereupon the closure expands to form an engagement surface. A piece of thread is secured to the closure through the body so that the closure can be pulled toward the puncture in the vessel in order to seal the same. No means are provided for accurately positioning the device relative to the puncture in the blood vessel.

U.S. Pat. No. 5,053,046 describes a spinal cannula device that seals a puncture in the spine created by the cannula. The device includes first and second cannulas, wherein the second cannula is inserted into the first and includes a dural seal with an absorbable suture extending therefrom. The first cannula effectuates the initial spinal puncture. Once the diagnostic or therapeutic procedure is accomplished, the second cannula is inserted into the first cannula until it extends through the puncture. A stylet is inserted into the inner cannula whereupon it pushes the seal and an absorbable suture into the cerebrospinal fluid. The seal absorbs liquid and swells. The cannulae are removed and the physician then pulls on the suture in order to set the dural seal in the spinal puncture. This device would not be effective for sealing an opening in a more flexible structure such as a blood vessel.

U.S. Pat. No. 5,021,059 describes a plug device for sealing punctures in tissue. The device includes a carrier that has an anchoring portion, a sealing portion and a thin filament connected therebetween. The carrier has an end that is adapted to fit through the puncture. In use, the anchoring portion is ejected through the puncture and is then drawn toward the free end of the carrier. The instrument is manipulated in order to draw the anchoring portion against the puncture on the inner surface of the tissue. To completely seal the puncture, the instrument is further manipulated to draw the sealing portion into engagement with the outer surface of the tissue on the opposite side of the anchoring portion. This is a relatively complicated device requiring a large amount of manipulation and a high degree of skill on the part of the user.

SUMMARY OF THE INVENTION

The present invention relates to a device and method for sealing an opening in an anatomical structure. The device includes a flexible tube including a proximal portion and a distal portion extending along a common axis. The proximal portion of the device is coupled to the distal portion of the device by a central portion, which extends from a distal end of the proximal portion to a proximal end of the distal portion. The central portion bends away from the axis along a curve so that the distal end of the proximal portion faces the proximal end of the distal portion across a gap formed by the central portion. When the device extends through the anatomical structure opening in an operative position, the wall of the anatomical structure is received within the gap. The device also includes first and second needle lumens extending through the proximal portion substantially parallel to the axis. The needle lumens extend from a proximal end of the proximal portion to an opening formed in the distal end of the proximal portion. The device further includes a needle receiving chamber that is formed in the distal portion. The needle receiving chamber extends from a third opening formed in the proximal end of the distal portion to a curved distal wall shaped so that, when a flexible needle enters the needle receiving chamber from the first needle lumen, the flexible needle curves along the distal wall to exit the needle receiving chamber at a point opposite the second needle lumen. Other conventional devices for sealing punctures in anatomical structures are also described in U.S. Pat. Nos. 5,304,184, 5,417,699 and 5,527,322.

BRIEF DESCRIPTION OF THE DRAWINGS

FIG. 1 shows a cross-sectional side view of a surgical suturing device according to an embodiment of the present invention.

FIG. 2A shows a cross-section of a device according to the present invention taken along line A—A of FIG. 1.

FIG. 2B shows a cross-section of a device according to the present invention taken along line B—B of FIG. 1.

FIG. 7 shows a cross-sectional magnification of the surgical device in the area of a center portion positioned at the wall of the blood vessel according to the present invention.

FIG. 8 shows the surgical device as shown in FIG. 7 with the tubes penetrating the target area of the blood vessel wall according to the present invention.

FIG. 9 shows the surgical device as shown in FIG. 7 with a length of suture extending through needle channels.

FIG. 10 shows the surgical device as shown in FIG. 8 with a length of suture extending through the tubes that penetrated the walls of the blood vessel.

FIG. 14 shows the other ends of the first and second lengths of sutures being pulled away from the opening in the wall of the blood vessel.

FIG. 15 shows the other ends of the first and second lengths of suture tied for moving toward the blood vessel.

FIG. 16 shows an instrument coupled to the suture loop knot and urging the loop knot toward the blood vessel.

FIG. 17 shows the suture sealing the puncture.

FIG. 18 shows a cross-sectional side view of a surgical suturing device according to another embodiment of the present invention.

FIG. 19 shows a cross-section of a device according to the present invention taken along line C—C of FIG. 18.

DETAILED DESCRIPTION

Figure 3:
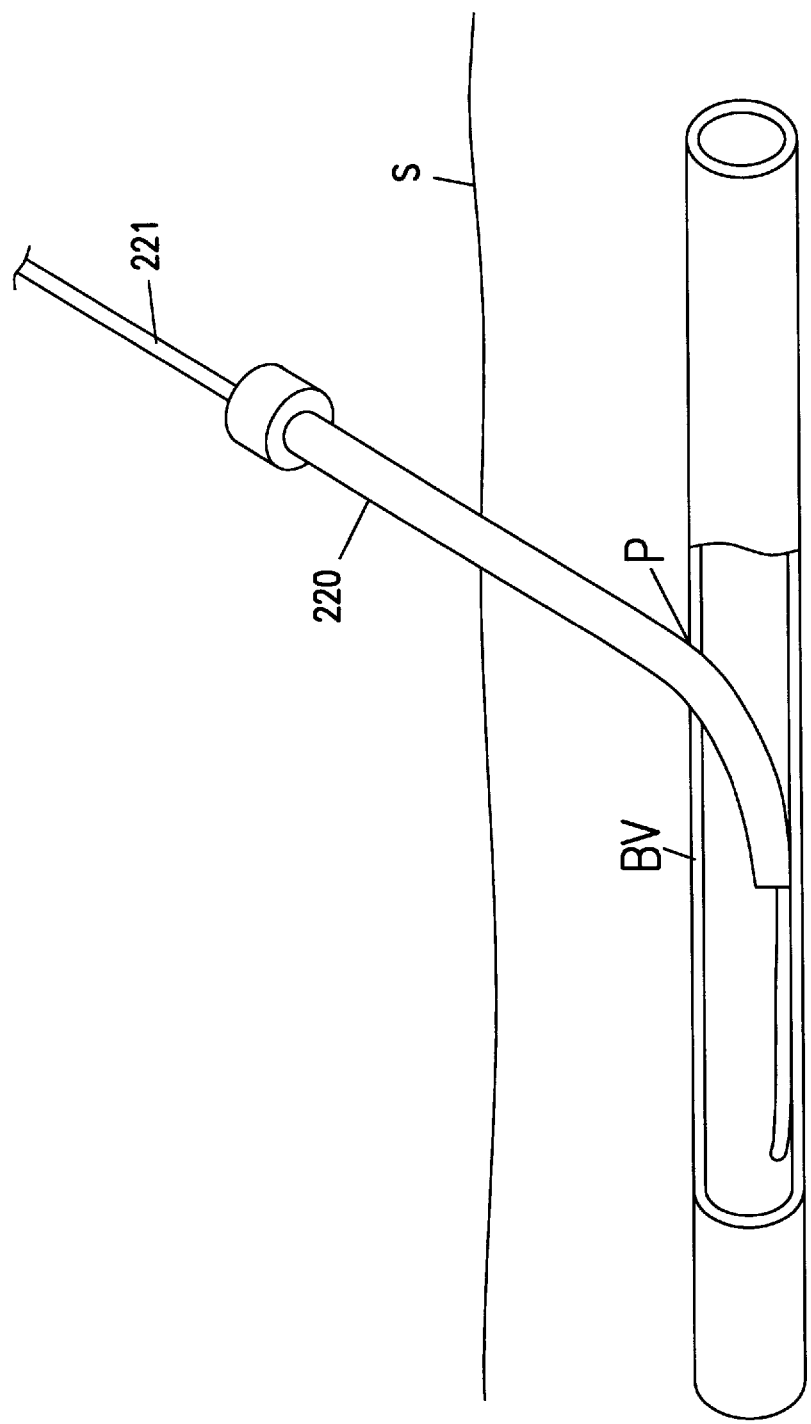
FIG. 3 shows a partially cross-sectional view of the introducer device extending a guide wire into the blood vessel.
Figure 4:
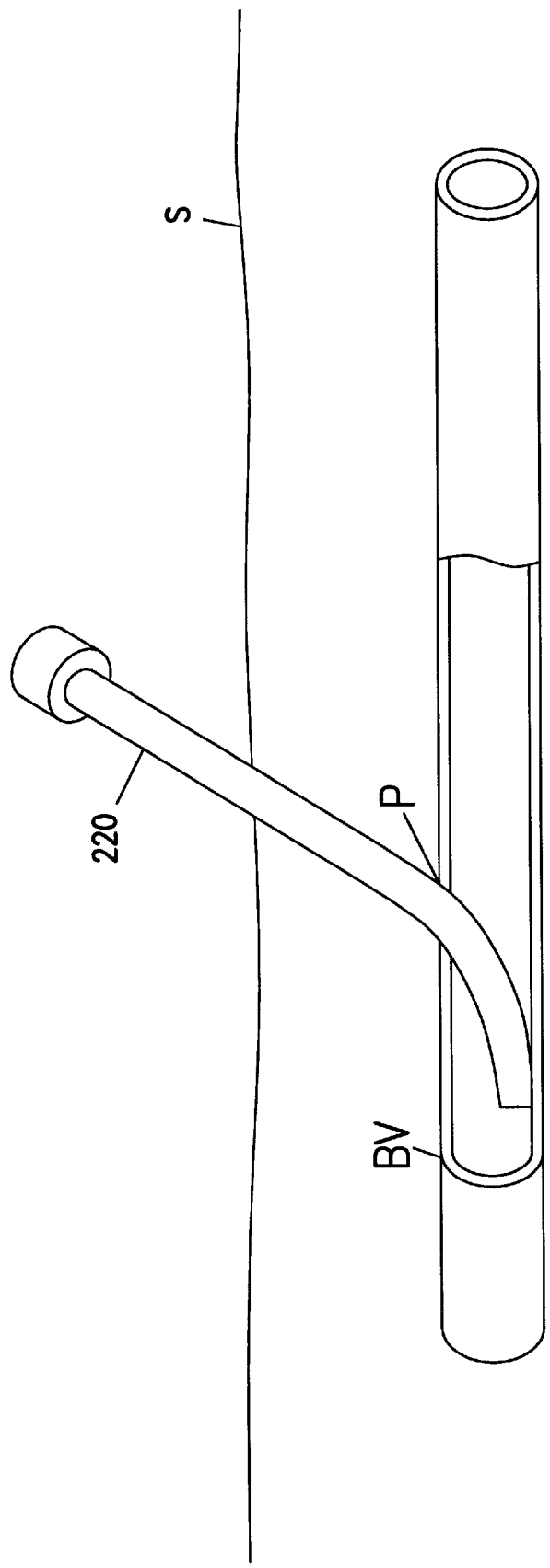
FIG. 4 shows a partially cross-sectional view of an introducer device penetrating a wall of the blood vessel.

FIG. 1 shows an embodiment of a device 201 according to the present invention for suturing punctures in blood vessels, internal organs and the like. The device 201 includes flexible tube 204 having, preferably, a circular or elliptical cross-section. The flexible tube 204 includes a proximal part 202 and a distal part 203. The proximal part 202 extends from a first end 205 through a curved central portion 206 to a second end 207 which mates with a proximal end 208 of the distal part 203. The curved central portion 206 may have a substantially circular or elliptical cross-section. The flexible tube 204 is preferably constructed of a thermoplastic material such as polyurethane, polyethylene, or the like, in two or three parts bonded together, as is known in the art. Various parts of the flexible tube 204 may preferably be either extruded or molded. It may be more economical to extrude the parts including one or two lumens, while other portions, i.e., curved sections of the flexible tube 204, may be more economically molded. The length and diameter of the flexible tube 204 may be pre-selected to comply with the requirements of a particular situation. The length may preferably be between 1" and 16", while the diameter may preferably be varied below 1". Tubes of other lengths may also be used as the situation demands. Other dimensions of the tube can also be conceivable.

The flexible tube 204 includes two needle guiding bores 210' and 210" (see FIGS. 7–10) extending through the proximal part 202 from the first end 205 to respective bore openings 211' and 211" (see FIGS. 7–10) at a proximal end 212 of the curved central portion 206. As shown in FIG. 2B, the two needle guiding bores 210' and 210" are each, preferably, circular in cross-section and may each include optional slot openings 212' and 212" to the outside of the flexible tube 204. A flashback lumen 219" is also provided to allow a user to determine when the device 201 is in a desired position. That is, when the blood flows out from the flashback lumen 219" and not out of needle guiding bores 210' and 210", a user will know that the blood vessel wall is received in the curved portion 206 with the flashback lumen opening into the blood vessel.

As shown in FIGS. 2A and 7, the second end 207 of the curved central portion 206 includes a suture return chamber 213 for receiving a flexible needle 214 (see FIGS. 9 and 10) and returning it to the proximal part 202. Specifically, the suture return chamber 213 extends from the curved end wall 300 to a proximal opening 215 formed opposite the slot openings 212' and 212". The needle guiding bores 210' and 210" are oriented so that a flexible needle 214 guided through one of the needle guiding bores (e.g., 210'), leaves a corresponding one of the bore openings (e.g., 211') and enters the suture return chamber 213. The needle travels along the wall of the suture return chamber 213 to the curved end wall 300, which is shaped (e.g. U-shaped) to slidably receive and reverse the direction of travel of the flexible needle 214 to pass around the suture return chamber (213 and enter the other one of the needle guiding bores (e.g., 210") via the other one of the distal openings (e.g., 211").

The flexible needle 214 may preferably be constructed of polyester material, between 2" and 12" in length and between 0.010" and 0.030" in diameter. The flexible needle 214 includes a distal sharp end 217 and a proximal suture end 218. A length of suture 216 is coupled to the proximal suture end 218 of the flexible needle 214.

Figure 5:
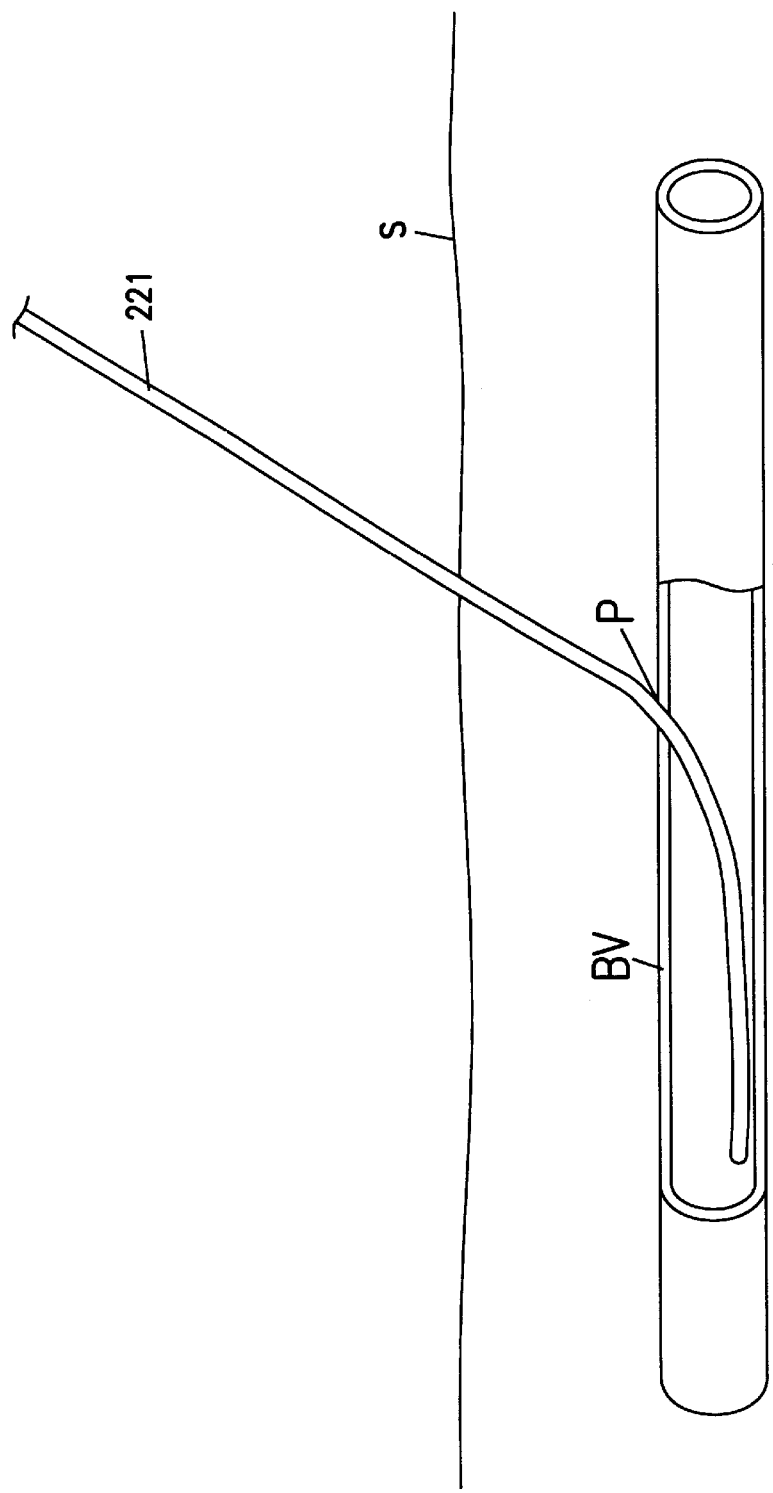
FIG. 5 shows a partially cross-sectional view of the guide wire after removing the introducer device from the blood vessel.
Figure 6:
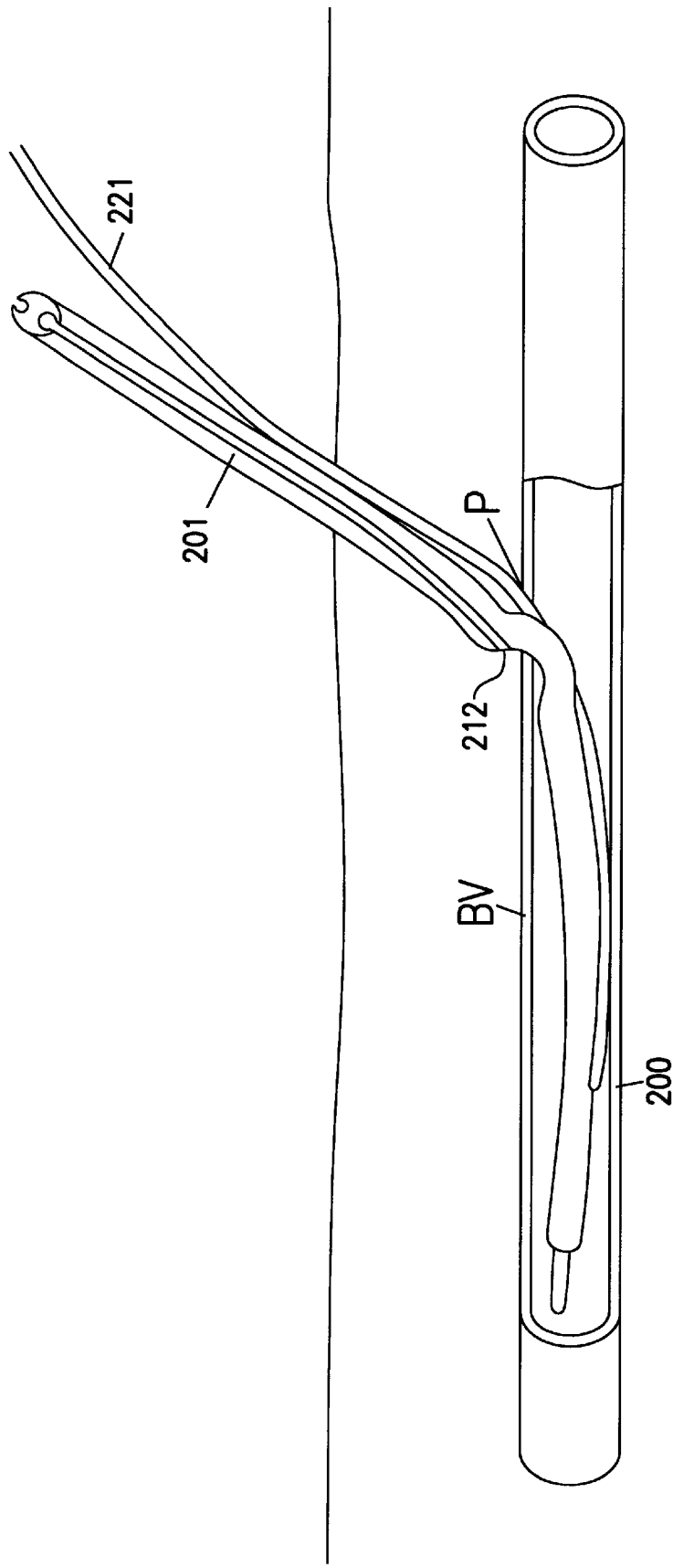
FIG. 6 shows a partially cross-sectional view of the blood vessel with the device according to the present invention received on the guide wire.

As shown in FIGS. 3–17, when an invasive procedure is performed on a patient which requires an insertion of a catheter into a blood vessel (or other structure within the body), an introducer sheath 220 is inserted through the skin S into the patient's body through a puncture P in a wall of the blood vessel BV (shown in FIG. 3). A guide wire 221 is inserted through the puncture P to the target area within the blood vessel and a catheter is inserted through the introducer sheath, over the guide wire 221, to a target area. After completing the procedure, the catheter and the introducer sheath 220 are withdrawn, and the guide wire 221 is left in the blood vessel BV (shown in FIG. 5). The proximal end of the guide wire 221 is then inserted through the guide wire lumen 200 and the device 201 is inserted into the body and moved along the guide wire 221 through the puncture P until the curved central portion 206 straddles a portion of the blood vessel wall adjacent to the puncture P.

By observing the flash back lumen 2191", which is fluidly coupled to a determining bore 219' situated in the center of the curved central portion 206, the user may determine when the device 201 is in the desired position. Specifically, when the device 201 is inserted far enough into the blood vessel, blood will be observed in the flash back lumen 219". The absence of blood flow through the needle guiding bores 210' and 210" at this time shows that the blood vessel wall is received between the distal opening of the flashback lumen 219" and the distal openings 211' and 211".

As the device 201 is inserted into the blood vessel, the flexible tube 204 bends so that the device 201 is received within, and extends in the direction of the blood vessel without straining the blood vessel. In this position, the distal central portion opening 215 is positioned on the distal side of the puncture P facing the proximal end 212 of the curved central portion 206, as shown in FIG. 7. The user may then extend optional guide tubes 225' and 225" through the corresponding guiding bores 210' and 210" from the proximal end 212 of the curved central portion 206, as illustrated in FIG. 8. Alternatively, the operation may be performed without the use of the guide tubes 225' and 225". Each of the guide tubes 225' and 225" penetrates a respective target area in the wall of the blood vessel and enters the suture return chamber 213 through the distal central portion opening 215 of the curved central part 206, thus providing a further guide surface for the flexible needle 214.

Then, as shown in FIG. 9, the user inserts the forward sharp end 217 of the flexible needle 214 through the first end 205 of the proximal part 202 through the needle guiding bore 210" and out through the corresponding bore opening 211". When the guide tubes 225' and 225" are used, the forward end 217 of the flexible needle 214 passes through the central bore of one of the guide tubes 225' and 225" to enter the suture return chamber 213. When the guide tubes 225' and 225" are not used, the forward sharp end 217 of the flexible needle 214 penetrates the target area in the wall of the blood vessel (corresponding to the distal opening 211") and enters the suture return chamber 213 through the distal central portion opening 215. The flexible needle 214 bends around the wall of the suture return chamber 213, and reverses its direction of slidable movement so that the forward sharp end 217 of the flexible needle 214 either enters the central bore of the other guide tube (225' or 225") or penetrates a second target area and then enters the other needle guiding bore 210' via the other distal opening 211'. The needle 214 then extends from the first end 205 of the proximal part 202, so that the length of suture 216 coupled to the proximal suture end 218 of the flexible needle 214 is drawn through the distal openings 211' and 211" and through the blood vessel wall.

Figure 11:
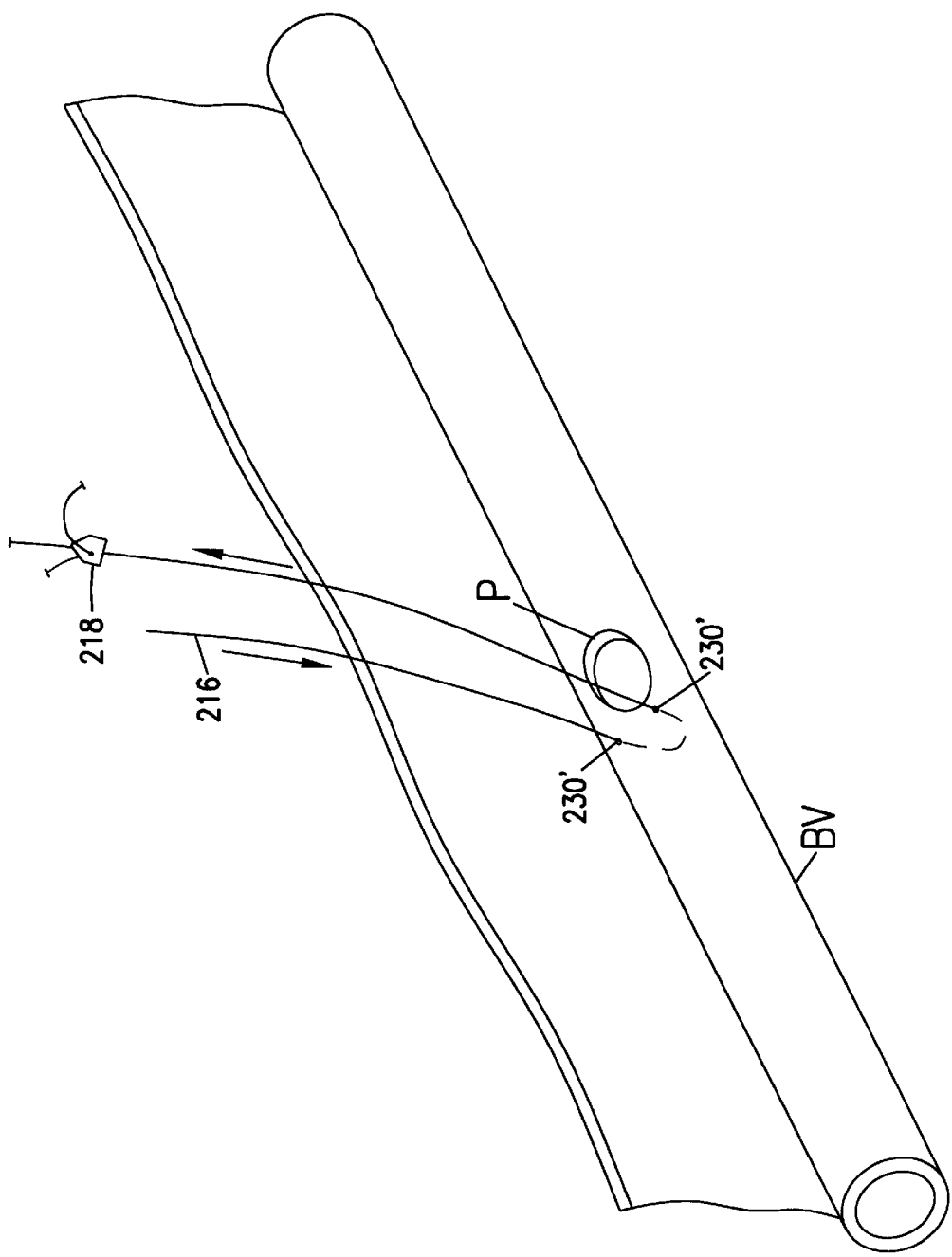
FIG. 11 shows a first length of suture extending through the punctures in the walls of the blood vessel that were made at a first position.

As shown in FIG. 11, when the flexible needle 214 is fully withdrawn from the device 201, the length of suture 216 extends (in a direction X) through penetrated areas 230' and 230" in the wall of the blood vessel BV. The user may then grasp the forward sharp end 217 of the flexible needle 214 and withdraw the flexible needle from the device 201 to draw the suture 216 through the blood vessel and out of the end 205 of the device 201.

Figure 12:
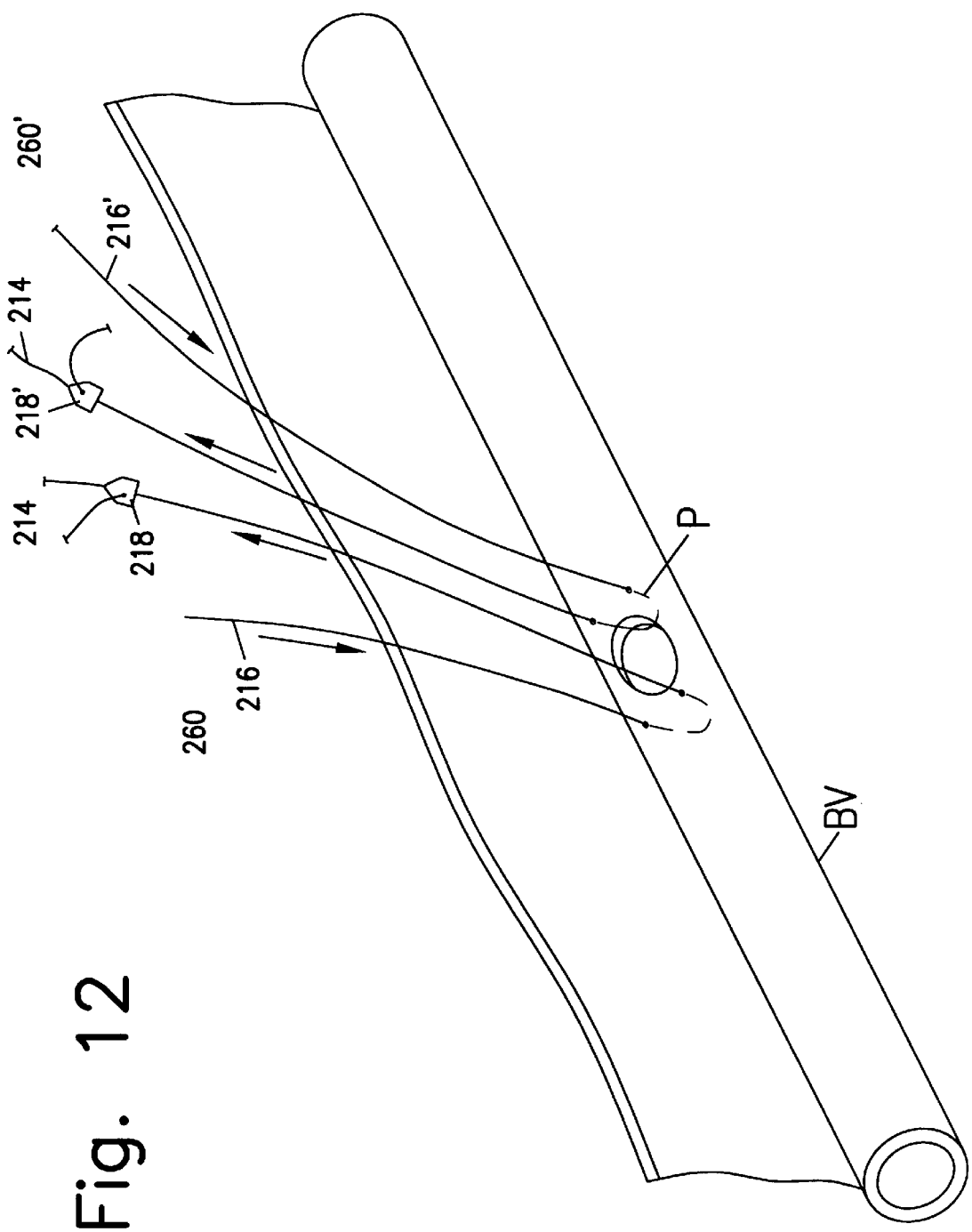
FIG. 12 shows the first length of suture extending through the punctures in the walls of the blood vessel that were made at the first position and a second length of suture extending through the punctures in the walls of the blood vessel that were made at a second position.
Figure 13:
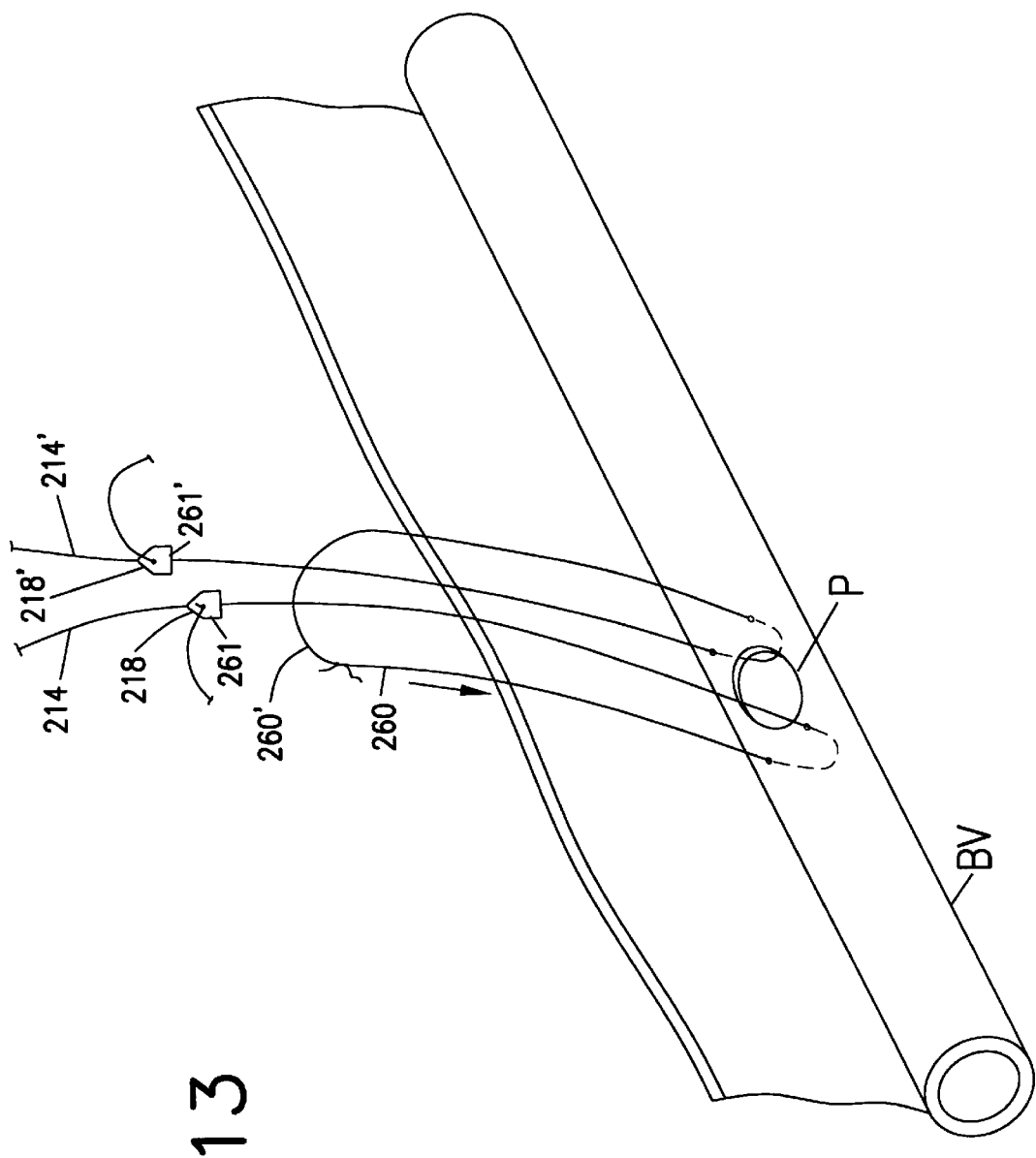
FIG. 13 shows a square knot tieing an end of the first length of suture with an end of the second length of suture creating a suture loop.

Thereafter, the user rotates the device 201 until the curved central portion 206 straddles the blood vessel wall in a second desired orientation, relative to the opening. Those skilled in the art will understand that this "desired position" will usually be on the opposite side of the puncture, so that the device 201 will be rotated approximately 180° after the previously inserted flexible needle 214 has been withdrawn from the device 201. When the device 201 is in the second desired orientation, the user performs a procedure substantially similar to that described above with respect to FIGS. 7–10, using another flexible needle 214' and another length of suture 216' attached to the proximal end thereof. Accordingly, two lengths of sutures 216 and 216' may be drawn through the blood vessel wall adjacent to the opening, as shown in FIG. 12.

As shown in FIGS. 13–17, the user ties free ends 260 and 260' of the corresponding lengths of sutures 216 and 216' (preferably the ends which are not connected to proximal suture ends 218 and 218' of the flexible needles 214 and 214') in a square knot which is urged inward toward the blood vessel and drawn tight in order to seal the puncture. Thereafter, the attached ends 260 and 260' of the corresponding lengths of sutures 216 and 216' are detached from the respective flexible needles 214 and 214', and also tied together. Those skilled in the art will appreciate that, once the lengths of the sutures 214 and 214' have been drawn through the blood vessel wall, various other methods of fastening the sutures together may be employed.

Another embodiment of the device 201' according to the present invention is shown in FIG. 18. This device 201' also includes flexible tube 204', which includes a proximal part 202' and a distal part 203'. The proximal part 202' extends from a first end 205' through a curved central portion 206' to the distal part 203'. The curved central portion 206' may also have a substantially circular or elliptical cross-section. The flexible tube 204' of this embodiment includes two needle guiding bores 305' and 305" extending from the corresponding proximal openings 301' and 301" of the proximal part 202' from the first end 205' and through the proximal part 202'. As shown in FIG. 19, the two needle guiding bores 305' and 305" are each, preferably, circular in cross-section. The needle guiding bore 305 extends to a first opening 302' at a proximal end 312 of the curved central portion 206', while the needle guiding bore 305" which also preferably functions as a flashback lumen, extends from the proximal opening 301" to a second opening 302". Thus, when blood flows from the needle guiding bore 305" and does not flow from the needle guiding bore 305', a user will know that the blood vessel wall is received within the curved central portion 206' with the needle guiding bore 305" opening situated inside the blood vessel. The curved central portion 206' includes a return part 303, adjacent to the second opening 302", which is positioned directly opposite to the first opening 302'.

In use, a user first inserts the device 201' into the blood vessel in a similar manner as the user may insert device 201 as described above in FIGS. 3–17. In particular, the device 201' is positioned so that the second opening 302" is positioned on a distal side of a puncture facing the first opening 302'. The user may then extend an optional guide tube as described in regard to the previous embodiments, from the first end 205' of the proximal part 202', through the first opening 302' to enter the needle guiding bore 305" at the second opening 302". The optional guide tube penetrates a target area in the wall of the blood vessel and enters the needle guiding bore 305" through the second opening 302" to provide a further guide surface for the insertion of a flexible needle into the needle guiding bore 305'. Alternatively, the operation may be performed without the use of the optional guide tube.

The user then inserts the forward sharp end 217 of a flexible needle 214 (shown, e.g., in FIG. 9) through the first end 205' of the proximal part 202', through the first opening 302' into the needle guiding bore 305" at the second opening 302". If the optional guide tube is used, the forward end 217 of the flexible needle 214 passes through the guide tube to enter a portion of the needle guiding bore 305". When the guide tube is not used, the forward sharp end 217 of the flexible needle 214 penetrates the target area in the wall of the blood vessel (adjacent to the first opening 302') and enters the needle guiding bore 305" through the second opening 302". The flexible needle 214 bends around the curved central portion 206', and reverses its direction of slidable movement so that the forward sharp end 217 of the flexible needle 214 returns through the needle guiding bore 305" to the proximal part 202' of the device. The flexible needle 214 extends from the first end 205' of the proximal part 202', so that the length of suture 216 coupled to the proximal suture end 218 of the flexible needle 214 (shown, e.g., in FIG. 9) is drawn through the first opening 302', through the blood vessel wall and into the second opening 305". After the forward sharp end 217 of the flexible needle 214 is drawn out from the first end 205' of the needle guiding bore 305", the user then grasps the forward sharp end 217 of the flexible needle 214 and withdraws the flexible needle from the device 201' to draw the suture through the blood vessel and out of the first end 205' of the device 201'.

Thereafter, the user rotates the device 201' until the curved central portion 206' straddles the blood vessel wall in a second desired orientation, relative to the opening. Those skilled in the art will understand that this "desired position" will usually be on the opposite side of the puncture, so that the device 201' will be rotated approximately 180° after the previously inserted flexible needle 214 has been withdrawn from the device 201'. When the device 201' is in the second desired orientation, the user performs a procedure substantially similar to that described above with respect to the device 201' shown in FIG. 18, using the same flexible needle with the same length of suture to form a loop and seal the puncture except that the user inserts the flexible needle through the proximal opening 301" into the needle guiding bore 305". The flexible needle wraps around the curved central portion 206' and exits through the second opening 302", passes through the blood vessel wall and enters the needle guiding bore 305' via the first opening 302'. The user then pushes the flexible needle further through the needle guiding bore 305' until a forward end of the flexible needle protrudes from the proximal opening 301'. Thus, a single length of suture is drawn through two locations in the blood vessel wall separated by 180°. Of course, those skilled in the art will understand that this procedure may also be done by inserting separate lengths of suture at each of the desired orientations around the puncture site and then fastening these lengths of suture together to seal the puncture, as shown in FIG. 12.

In another embodiment of the present invention, the procedure substantially similar to that described above with respect to the device 201' shown in FIG. 18 is utilized at the second desired orientation using another flexible needle with another length of suture attached to the proximal end thereof. In this embodiment, two lengths of sutures may be drawn through the blood vessel wall adjacent to the opening. The attached ends of the corresponding lengths of sutures are detached from the respective flexible needles. Then, the free suture ends are coupled together and drawn tight in order to seal the puncture. Those skilled in the art will appreciate that, once the lengths of the sutures have been drawn through the blood vessel wall, various methods of fastening the sutures together in addition to knotting may be employed.

In addition, the user may thereafter rotate the device 201' to a third position, and then to a fourth position, while performing a procedure substantially similar to that described above. Those skilled in the art will also understand that the third desired position is preferably rotated approximately 90° from the second desired position, and the fourth desired position is preferably rotated approximately 180° from the third desired position.

What is claimed is:

1. A device for sealing an opening in a wall of an anatomical structure comprising:
    a tube including a proximal portion and a distal portion extending along a common central axis, wherein the proximal portion is coupled to the distal portion by a central portion, the central portion extending from a central portion proximal end that is coupled to a distal end of the proximal portion to a central portion distal end that is coupled to a proximal end of the distal portion, wherein a central axis of the central portion bends away from the common central axis along a curve so that the distal end of the proximal portion faces the proximal end of the distal portion across a gap formed by the central portion with the common central axis extending between the proximal and distal portions through the gap, wherein, when the device extends through the opening in an operative position, the wall of the anatomical structure is received within the gap;
    a first needle lumen extending through the proximal portion substantially parallel to the common central axis from a proximal end of the proximal portion to a first opening formed in the distal end of the proximal portion;
    a second needle lumen extending through the proximal portion substantially parallel to the common central axis from a proximal end of the proximal portion to a second opening formed in the distal end of the proximal portion; and
    a needle receiving chamber formed in the distal portion, the needle receiving chamber extending from a third opening formed in the proximal end of the distal portion to a distal wall extending from a first point opposite the first needle lumen around a curve to a second point opposite the second needle lumen so that, when a flexible needle enters the needle receiving chamber from the first needle lumen, the flexible needle curves along the distal wall to exit the needle receiving chamber at a point opposite the second needle lumen.

2. The device according to claim 1, further comprising:
    a flash-back lumen extending from the proximal end of the proximal portion through the proximal portion and into the central portion to a flash-back opening formed in the central portion.

3. The device according to claim 1, wherein the needle receiving chamber is substantially U-shaped in cross-section and wherein lines tangent to the curved distal wall at the first and second points extend substantially parallel to the axis.

4. The device according to claim 1, wherein the needle receiving chamber includes two substantially straight sides extending proximally from the first and second points respectively, and wherein each of the two straight sides of the needle receiving chamber is substantially aligned with one of the first and second openings.

5. The device according to claim 1, wherein the flexible tube is composed of a thermoplastic material.

6. The device according to claim 1, wherein device is formed of two pieces bonded together.

7. The device according to claim 1, wherein at least a portion of the flexible tube is one of a circular and an elliptical in cross-section.

8. The device according to claim 1, wherein, when the device extends through the anatomical structure opening in the operative position, a flexible needle inserted into the proximal end of the proximal portion through the first needle lumen will penetrate the anatomical structure at a first penetrating location and enter the needle receiving chamber.

9. The device according to claim 4, wherein the sides and the curved distal wall of the needle receiving chamber are oriented so that a flexible needle entering the needle receiving chamber from the first needle lumen slides along a first of the sides of the needle receiving chamber, around the curved distal wall to a second of the sides to exit the needle receiving chamber to penetrate the anatomical structure at a second penetrating location and extend into the second needle lumen.

10. The device according to claim 1, further comprising:
    first and second guide tubes, each of the first and second guide tubes being slidably received within a respective one of the first and second needle lumens.

11. The device according to claim 10, wherein the first guide tube is extendable by a user from a first position in which a distal end of the first guide tube is received in the first needle lumen to a second position in which the distal end of the first guide tube is received in the needle receiving chamber.

12. A method for sealing an opening of an anatomical structure within a living body, comprising the steps of:
    guiding into the opening a device including:
        a flexible tube having a proximal portion and a distal portion extending along a common central axis, the proximal portion being coupled to the distal portion by a central portion, wherein a central axis of the central portion curves away from the common central axis to form a gap between a distal end of the proximal portion and a proximal end of the distal portion, and wherein the common central axis extends between the proximal and distal portions through the gap, first and second needle lumens, each extending through the proximal portion substantially parallel to the common central axis to a respective lumen opening formed in the distal end of the proximal portion, and a needle receiving chamber formed in the distal portion extending from a proximal end of the distal portion to a curved distal wall;

positioning the device in a first desired orientation so that a first portion of a wall of the anatomical structure is received within the gap formed by the curved central portion, so that each of the lumen openings is positioned on a side of the anatomical structure opposite to the needle receiving chamber;

projecting, through the first needle lumen, a first flexible needle coupled to a first length of suture, so that a first sharp forward end of the first flexible needle passes through the anatomical structure wall at a first location and enters the needle receiving chamber;

thereafter, further projecting the first flexible needle around the curved distal wall of the needle receiving chamber to exit the needle receiving chamber, pierce the anatomical structure wall at a second location spaced from the first location, and enter the second needle lumen;

extracting the first flexible needle from the second needle lumen to draw the first length of suture through the anatomical structure wall to extend from the device;

rotating the device within the opening to a second desired orientation so that a second portion of the wall of the anatomical structure is received within the gap;

projecting a second flexible needle coupled to a second length of suture through the first needle lumen, so that a sharp forward end of the second flexible needle passes through the anatomical structure at a third location and enters the needle receiving chamber;

thereafter, further projecting the second flexible needle around the curved distal wall of the needle receiving chamber to exit the needle receiving chamber, pierce the wall of the anatomical structure at a fourth location spaced apart from the third location, and enter the second needle lumen;

coupling the first and second lengths of suture to seal the anatomical structure opening.

13. The method according to claim 12, wherein the device further includes at least two guide tubes corresponding to the needle lumens, each guide tube being slidably received within a respective one of the first and second needle lumens.

14. The method according to claim 13, wherein, prior to the step of projecting a first flexible needle, the user performs the steps of:

extending a first one of the two guide tubes through the respective needle lumen to pierce the anatomical structure wall at the first location and enter the needle receiving chamber; and extending a second one of the two guide tubes through the respective needle lumen to pierce the anatomical structure wall at the third location and enter the needle receiving chamber.

15. The method according to claim 14, wherein prior to the step of rotating the device to the second desired orientation, the user performs the step of:

retracting each of the two guide tubes into the respective one of the first and second needle lumens.

16. A device for sealing an opening in a wall of an anatomical structure comprising:

a flexible tube including a proximal portion and a distal portion extending along a common central axis, wherein the proximal portion is coupled to the distal portion by a central portion, the central portion extending from a central portion proximal end that is coupled to a distal end of the proximal portion to a central portion distal end that is coupled to a proximal end of the distal portion, wherein a central axis of the central portion bends away from the common central axis along a curve so that the distal end of the proximal portion faces the proximal end of the distal portion across a gap formed by the central portion with the common central axis extending between the proximal and distal portions through the gap, wherein, when the device extends through the opening in an operative position, the wall of the anatomical structure is received within the gap;

a first needle lumen extending through the proximal portion substantially parallel to the common central axis from a proximal end of the proximal portion to a first opening formed in the distal end of the proximal portion; and a second needle lumen extending through the proximal portion substantially parallel to the common central axis from a proximal end of the proximal portion, around the curve of the central portion to a second opening formed in the proximal end of the distal portion, the second opening facing the first opening, so that when a flexible needle is passed through the first needle lumen to exit from the first opening, the flexible needle crosses the gap and enters the second opening.

17. A method for sealing an opening of an anatomical structure within a living body, comprising the steps of:

guiding into the opening a device including:

a flexible tube having a proximal portion and a distal portion extending along a common central axis, the proximal portion being coupled to the distal portion by a central portion, wherein a central axis of the central portion curves away from the common central axis to form a gap between a distal end of the proximal portion and a proximal end of the distal portion, with the common central axis extending between the proximal and distal portions through the gap, a first needle lumen extending through the proximal portion substantially parallel to the common central axis to a first opening formed in the distal end of the proximal portion, and a second needle lumen extending through the proximal portion substantially parallel to the common central axis from a proximal end of the proximal portion, around the curve of the central portion to a second opening formed in the proximal end of the distal portion, the second opening facing the first opening;

positioning the device in a first desired orientation so that a first portion of a wall of the anatomical structure adjacent to the opening of the anatomical structure is received within the gap, so that the first opening is positioned on a proximal side of the wall of the anatomical structure and the second opening is positioned on a distal side of the wall of the anatomical structure;

projecting a flexible needle coupled to a first length of suture through the first needle lumen, so that a forward end of the flexible needle passes through the wall of the anatomical structure at a first location;

thereafter, further projecting the flexible needle to enter the second needle lumen through the second opening;

extracting the flexible needle from the second needle lumen to draw the first length of suture through the anatomical structure and out of the device;

rotating the device within the opening of the anatomical structure to a second desired orientation so that a second portion of the wall of the anatomical structure is received within the gap;

projecting the flexible needle coupled to a second length of suture through the first needle lumen, so that a forward end of the flexible needle passes through the anatomical structure at a second location;

thereafter, further projecting the flexible needle to enter the second needle lumen through the second opening;

extracting the flexible needle from the second needle lumen to draw the second length of suture through the anatomical structure; and coupling the first and second lengths of suture together to seal the opening of the anatomical structure.

18. A method for sealing an opening of an anatomical structure within a living body, comprising the steps of:

guiding into the opening a device including:

a flexible tube having a proximal portion and a distal portion extending along a common central axis, the proximal portion being coupled to the distal portion by a central portion, wherein a central axis of the central portion curves away from the common central axis to form a gap between a distal end of the proximal portion and a proximal end of the distal portion, a first needle lumen extending through the proximal portion substantially parallel to the common central axis to a first opening formed in the distal end of the proximal portion, and a second needle lumen extending through the proximal portion substantially parallel to the common central axis from a proximal end of the proximal portion, around the curve of the central portion to a second opening formed in the proximal end of the distal portion, the second opening facing the first opening;

positioning the device in a first desired orientation so that a first portion of a wall of the anatomical structure adjacent to the opening of the anatomical structure is received within the gap, so that the first opening is positioned on a proximal side of the wall of the anatomical structure and the second opening is positioned on a distal side of the wall of the anatomical structure;

projecting a flexible needle coupled to a length of suture through the first needle lumen, so that a forward end of the flexible needle passes through the wall of the anatomical structure at a first location;

thereafter, further projecting the flexible needle to enter the second needle lumen through the second opening;

extracting the flexible needle from the second needle lumen to draw the length of suture through the anatomical structure and out of the device;

rotating the device within the opening of the anatomical structure to a second desired orientation so that a second portion of the wall of the anatomical structure is received within the gap;

projecting the flexible needle coupled to the length of suture through the second needle lumen, so that a forward end of the flexible needle passes through the anatomical structure at a second location;

thereafter, further projecting the flexible needle to enter the first needle lumen through the first opening;

extracting the flexible needle from the first needle lumen to draw the length of suture through the anatomical structure; and coupling a first end of the length of suture to a second end of the length of suture to seal the opening of the anatomical structure.

19. A device for sealing an opening in a wall of an anatomical structure comprising:

a tube including a proximal portion and a distal portion extending along a common central axis, wherein the proximal portion is coupled to the distal portion by a central portion, the central portion extending from a central portion proximal end that is coupled to a distal end of the proximal portion to a central portion distal end that is coupled to a proximal end of the distal portion, wherein a central axis of the central portion bends away from the common central axis along a curve so that the distal end of the proximal portion faces the proximal end of the distal portion across a gap with the common central axis extending between the proximal and distal portions through the gap, wherein, when the device extends through the opening in an operative position, the wall of the anatomical structure is received within the gap;

a first needle lumen extending through the proximal portion substantially parallel to the common central axis from a proximal end of the proximal portion to a first opening formed in the distal end of the proximal portion;

a second needle lumen extending through the proximal portion substantially parallel to the common central axis from a proximal end of the proximal portion to a second opening formed in the distal end of the proximal portion; and a needle receiving chamber formed in the distal portion, the needle receiving chamber extending from a third opening formed in the proximal end of the distal portion to a distal wall shaped so that, when a flexible needle enters the needle receiving chamber from the first needle lumen, the flexible needle curves along the distal wall to exit the needle receiving chamber at a point opposite the second needle lumen, wherein sides of the curved distal wall are oriented so that a flexible needle entering the needle receiving chamber from the first needle lumen slides along a first of the sides of the needle receiving chamber, around the curved distal wall to a second of the sides to exit the needle receiving chamber to penetrate the anatomical structure at a second penetrating location and extend into the second needle lumen.

* * * * *